(12) United States Patent
Babichenko (10) Patent No.: US 9,863,887 B2
(45) Date of Patent: Jan. 9, 2018

(54) UNIT AND METHOD FOR OPTICAL NON-CONTACT OIL DETECTION

(71) Applicant: NEMOR TECHNOLOGIES OÜ, Tallinn (EE)

(72) Inventor: Sergey Babichenko, Tallinn (EE)

(73) Assignee: NEMOR TECHNOLOGIES OU, Tallinn (EE)

( * ) Notice: Subject to any disclaimer, the term of this patent is extended or adjusted under 35 U.S.C. 154(b) by 163 days.

(21) Appl. No.: 14/441,264

(22) PCT Filed: Nov. 15, 2012

(86) PCT No.: PCT/EP2012/072665
§ 371 (c)(1),
(2) Date: May 7, 2015

(87) PCT Pub. No.: WO2014/075724
PCT Pub. Date: May 22, 2014

(65) Prior Publication Data
US 2015/0293032 A1    Oct. 15, 2015

(51) Int. Cl.
*G01N 21/64* (2006.01)
*G01N 21/94* (2006.01)

(52) U.S. Cl.
CPC ............. *G01N 21/94* (2013.01); *G01N 21/64* (2013.01); *G01N 2021/6421* (2013.01);
(Continued)

(58) Field of Classification Search
None
See application file for complete search history.

(56) References Cited

U.S. PATENT DOCUMENTS

| 4,394,573 A | 7/1983 | Correa et al. |
| 5,096,293 A | 3/1992 | Cecchi et al. |

(Continued)

FOREIGN PATENT DOCUMENTS

| CN | 101 398 380 A1 | 4/2009 |
| FR | 2 972 260 A1 | 9/2012 |

(Continued)

OTHER PUBLICATIONS

English_Abstract_of_CN101398380A.
(Continued)

*Primary Examiner* — Shawn Decenzo
(74) *Attorney, Agent, or Firm* — Ladas & Parry LLP (57) ABSTRACT

The invention relates to a unit and method for detection of presence of oil on the water surface or in the water column. Unit comprises a sensor, whereby the sensor is connected to electronic compartment followed by microprocessor controller with embedded software for carrying out necessary analyses of reflected signals received by the sensor. The microprocessor controller is connected to communication means for transmitting an alarm signal through external communication line in case of oil pollution. All elements mentioned above are supplied by external power supply and are accommodated into a waterproof housing. The sensor comprises the probe light source formed by a pulsed UV LED, collimating optics and narrow band optical filter, at least one dichroic mirror, a projection-receiving lens, at least one optical filter, at least one photodetector and a reference photodetector.

12 Claims, 7 Drawing Sheets

(52) U.S. Cl.
CPC . *G01N 2021/945* (2013.01); *G01N 2201/021* (2013.01); *G01N 2201/061* (2013.01); *G01N 2201/062* (2013.01); *G01N 2201/0625* (2013.01); *G01N 2201/0696* (2013.01)

(56) References Cited

U.S. PATENT DOCUMENTS

| | | | | |
|---|---|---|---|---|
| 5,406,082 | A * | 4/1995 | Pearson | G01B 11/0625 250/301 |
| 5,461,236 | A * | 10/1995 | Gram | G01N 21/64 250/301 |
| 5,604,582 | A * | 2/1997 | Rhoads | G01J 3/2823 250/458.1 |
| 5,639,668 | A * | 6/1997 | Neel | G01N 21/6428 385/12 |
| 6,953,262 | B2 * | 10/2005 | Cleaver | F21S 4/26 362/219 |
| 7,688,428 | B2 * | 3/2010 | Pearlman | G01J 3/02 356/70 |
| 2008/0037006 | A1 * | 2/2008 | Canas Triana | E21B 47/102 356/73 |
| 2009/0189074 | A1 * | 7/2009 | Bello | G01J 3/4406 250/301 |
| 2012/0201463 | A1 * | 8/2012 | Suzuki | G01J 3/10 382/192 |

FOREIGN PATENT DOCUMENTS

| | | |
|---|---|---|
| GB | 2 129 125 | 5/1984 |
| JP | 2005-030839 A | 2/2005 |
| WO | WO 93/25891 A1 | 12/1993 |
| WO | WO 2012/015332 | 2/2012 |

OTHER PUBLICATIONS

English_Abstract_of_JP2005030839A.
English_Abstract_of_FR2972260A1.
English_Abstract_of_WO2012015332A1.

* cited by examiner

FIG 7

UNIT AND METHOD FOR OPTICAL NON-CONTACT OIL DETECTION

TECHNICAL FIELD

The present invention relates to a unit and method for detection of presence of oil on the water surface or in the water column.

BACKGROUND ART

In-time detection of water pollution by oil remains a relevant task to prevent environmental damage due to the spill and pollution spreading and loss of the product caused by the leak incidents. Among the variety of the techniques used for the task, the most demanded are the ones capable of operating in real-time, unattended, and with minimal maintenance.

The Light Induced Fluorescence (LIF) is well known high sensitive method used for detection of oil in water. It is referred to as an active method due to the use of controlled light source. The selectivity of oil detection with this method is provided due to the fact that at properly selected spectrum of the inducing light the poly-aromatic hydrocarbons (PAH) of oil products produce fluorescence with specific spectral profile. This profile differs from spectral response of other materials to the same inducing light and due to that can be used for oil detection and quantification.

Another feature of the LIF method is that it can be applied remotely without sampling or contacting the water body. This feature in combination with high selectivity, sensitivity and instantaneous detection allows building the sensor based on LIF method operating continuously in non-contact and real-time mode.

LIF method is effectively realized for oil detection by airborne and shipboard LIDAR (Light Detection and Ranging) monitoring systems. These systems provide high sensitivity and spatial resolution down to meter scale and are capable to detect oil on the water surface, submerged oil, and dissolved and emulsified fractions. Being very effective as mobile units, such systems are often too complex and expensive for continuous local on-site monitoring.

The remote (non-contact) mode of oil detection with LIF method is realized by fluorescence LIDARs (Light Detection and Ranging). The invention according to patent document U.S. Pat. No. 5,096,293 "Differential fluorescence LIDAR and associated detection method" to Cecchi Giovanna, Pantani Luca, 1992 discloses the use of fluorescence LIDAR for real-time remote sensing, and in particular for remote sensing of water. The detection method is based on the inducing the emission of fluorescence radiation from a remote target and collecting such emission with following separation into plurality of predetermined spectral channels. Collected spectral signals are processed in a way of calculating the ratio of each channel signal to each other signal thus providing a form of ratios which is compared further with predetermined stored signals corresponding to defined targets or categories of targets. The method is realized by the system comprised the pulsed laser with optical means to direct the laser beam to the object and to collect back scattered radiation; optical channel separator means for separating a backscattered fluorescence signal into predefined number of channels, and signal processing means for forming a plurality of ratio signals and comparing the value of each ratio signal to values stored in a memory.

In the patent document WO2012015332 "Method for remote detection of oil pollution on the surface of water", to Belov, Mikhail Leonidovich et al, 2012 there is described a method for oil detection by irradiating the surface of the water in the ultraviolet range at the excitation wavelength and recording the intensity of the fluorescent radiation in two narrow spectral ranges with centers at wavelengths $\lambda_1$, $\lambda_2$. The wavelengths are selected from the condition for the maximum difference between the value of the radiation intensity ratio (for petroleum products) and the value of the radiation intensity ratio (for water). The measured value for the radiation intensity ratio is compared with threshold values.

The above method is based on the assumption that it is possible to define two wavelengths of fluorescence emission of oil with distinct ratio of intensities compared with that of pure water. Such an assumption does not work in case of oil products having the fluorescence in too distinguishing spectral ranges. For example, at the excitation wavelength 308 nm light oil (gasoline) has a max fluorescence at the emission wavelength 380 nm, and heavy oil (ship fuel) has a max fluorescence at the wavelength 520 nm. There is no any pair of wavelengths providing ratio of intensity distinguishing from clean water and equally usable for detection of both mentioned type of oils.

There is an invention defined in U.S. Pat. No. 7,688,428 "Non-contact oil spill detection apparatus and method" to Pearlman; Michael D, 2010 describing a non-contact sensor for oil spill detection based on LIF method.

The invention in U.S. Pat. No. 7,688,428 claims the oil detection method based on the anomalous signal return when oil is present compared with the signal when oil is absent. As the invention does not specify any means for taking into account ambient light and minimizing its influence, one can assume that the variation of ambient light due to glint reflection of sun light from the water surface could produce anomalous increase of the signal in the spectral range 320-400 nm and therefore the method will produce false alarm. As the method does not specify the data analysis, one can assume registering the anomalous signals caused by other than oil light reflecting materials on water surface, also possibly producing false alarms.

The sensor of U.S. Pat. No. 7,688,428 is based on the pulsed light source to produce a beam of light having the apex angle 13-15 degrees and spectrally limited to wavelengths between 225 and 300 nm, which is directed to the water; sensor means for detecting fluorescent light filtered in the spectral range between 320 to 400 nm, means for analyzing data and reporting and/or producing a signal or alarm when analyzed data indicates the presence of any significant amount of oil pollutant. The invention in U.S. Pat. No. 7,688,428 claims that high power strobed Xe lamp serves as a light source. The sensor is operated vertically above the water at the distance of 3 to 5 m from the surface and at the angle not more than 7 degrees from vertical. The invention also claims the method of oil detection predicated upon differential measurement, i.e. based on the anomalous signal return that will occur when oil is present, as opposed to when there are no hydrocarbons present.

The sensor described in U.S. Pat. No. 7,688,428 has the following limitations.
1) Using powerful Xe-lamp as a light source makes the sensor bulky and power consuming, causing principal limitations of the detection distance due to significant beam divergence (light beam has a shape of cone with apex angle 13-15 degrees), increase of the distance will require unreasonable increase of the power consumption.
2) Inclination of the incidence beam of about 7 degree of vertical to detect sufficient amount of fluorescent flux at the detector indicates that the optical axes of the sensing light beam and detection means do not coincide. The signal detection with optical scheme having misaligned optical axes of the light beam and optical axis of receiving means (bi-static optical layout) is exposed to the distance variation. Therefore even if the sensor is adjusted for the distance to water (for example 3-5 m), the change of the distance due to tides, waves or other processes will cause the fluctuations of fluorescence signal thus influencing the reliability of detection.

3) Due to above described reason the sensor cannot operate at the inclination angle more than 10 degrees from vertical. It limits its installation requirements and hampers operation in scanning mode when the inclination angle is varied.

Figure 2:
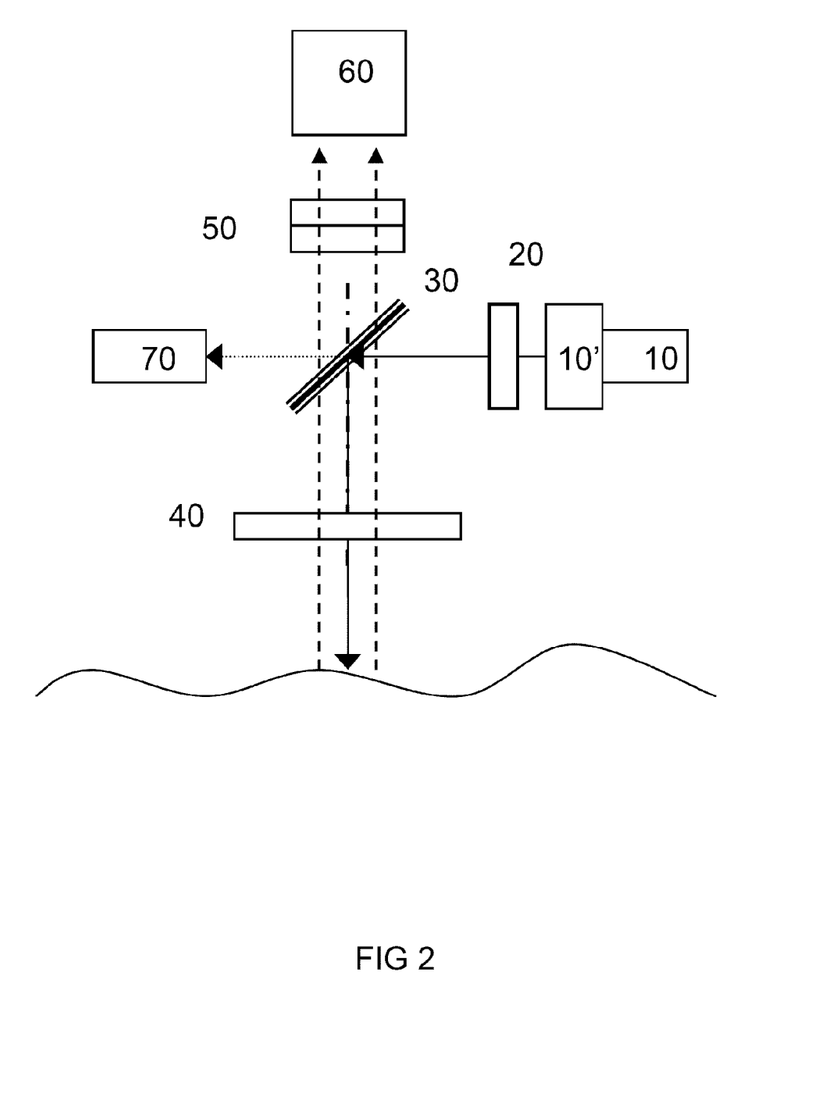
FIG. 2 shows a first version of an optical layout of the sensor indicated by reference number 2 in FIG. 1.

4) The detection limited to the spectral range 320-400 nm does not allow detection of oil products fluorescing at longer wavelengths (FIG. 2).

DISCLOSURE OF INVENTION

The present invention provides a unit for optical non-contact continuous detection of presence of light, medium and heavy oil products on water.

A unit according to present invention includes a sensor, which is connected to electronic compartment followed by microprocessor controller with embedded software for carrying out necessary analyses of returned signals received by the sensor unit. The microprocessor controller is connected to the communication means for transmitting an alarm signal through external communication line in case of oil pollution, whereby all the above elements are supplied by external power supply and accommodated into a waterproof housing.

The sensor comprises the probe light source formed by a pulsed UV LED, collimating optics and narrow band optical filter. The sensor unit also comprises at least one dichroic mirror, a projection-receiving lens, at least one optical filter, at least one photodetector, and a reference photodetector.

The probe light beam generated by UV LED (10) is guided by collimating optics through the narrow band optical filter onto the dichroic mirror, wherein minor part of said probe light beam is passed through said dichroic mirror into the reference photo detector. The reference photo detector registers the intensity signal of probe light beam generated by UV LED. Said dichroic mirror deflects the major part of probe light beam through projection-receiving lens onto the water surface such that said deflected probe light beam is coaxial with the axis of said projection-receiving lens.

The cut off wavelength of the dichroic mirror is selected such that dichroic mirror reflects UV LED light pulses having wavelength in UV spectral region shorter than cut off wavelength of the dichroic mirror. It passes through the return light in the spectral region of longer wavelengths than the cut off wavelength of the dichroic mirror.

Optical filter is a multi band optical filter passing through induced fluorescent flux of light, medium and heavy oil products and suppressing all other spectral components in the return light flux.

The sensor comprises at least one photodetector to register said filtered return light flux.

The sensor may comprise at least two separate photodetectors, whereby each photodetector having its own long pass optical filter. Return light is divided for each of said photodetectors by at least one beam splitter. In such schematics the differential signal of two detectors is due to the returned light flux in the spectral range limited by two cut-off wavelengths of long pass optical filters. This range can be adjusted by selecting proper cut off wavelengths to register induced fluorescence of specified light, medium or heavy oil products.

The sensor may also comprise three separate photodetectors, each photodetector is coupled with the narrow band optical filter. The passing spectral ranges of narrow band optical filters are selected such that first narrow band optical filter coupled with first photodetector passes through induced fluorescence flux in the spectral range for the light oil products. The second narrow band optical filter coupled with second photodetector passes through induced flux in the spectral range for the medium oil products. The third optical filter coupled with third photodetector passes through induced fluorescence flux in the spectral range for the heavy oil products.

The photodetector may consist from an assembly of photodetectors like an array or a matrix, every detector element of N photodetectors is aligned with the optical filter, providing multichannel spectral detection of the fluorescence.

The sensor according to the invention is scannable up to 45 degrees from a vertical position.

The unit according to the invention has a waterproof and hermetic housing filled with neutral gas at overpressure, providing additional safety of exploitation and protecting optical and electronic components from condensed humidity.

The present invention also provides a method for optical non-contact continuous detection of presence of oil products in the water. According to the method of present invention the light beam pulses are generated continuously with the UV LED and guided by the collimating optics through the optical filter onto the dichroic mirror. From the dichroic mirror the light beam pulses are guided through the optics onto the water. Induced light is guided through the optics into the sensor means for registering signals returned from monitored water surface. Part of each said probe light beam pulse generated by the UV LED is passed though said dichroic mirror into the reference photo detector for registering a signal of the intensity of the probe light beam generated by UV LED pulse. Part of each probe light beam pulse generated by the UV LED is deflected coaxially with the axis of the projection-receiving lens by said dichroic mirror through said projection-receiving lens onto the water surface. Synchronously with each probe light beam pulse a return light signal is collected and passed by the same projection-receiving lens through said dichroic mirror onto the means for registering return light signal.

A return light informative signal is obtained by normalizing return light signal using a signal of the intensity of the probe light beam generated by the UV LED pulse. Between consecutive probe light beam pulses generated by the UV LED a background light signal due the ambient light is registered with the help of the sensor means. Said background light signal is subtracted from the return light informative signal in order to obtain a differential signal. The obtained differential signal levels as an accumulated signal per multiple pulses N of UV LED are compared with the predetermined threshold signal level. An alarm signal is generated when predetermined threshold signal level and duration of time interval limit for consecutive warnings is exceeded.

BRIEF DESCRIPTION OF DRAWINGS

The invention is explained in detail below with reference to the drawings, in which.

MODE(S) FOR CARRYING OUT THE INVENTION

The present invention provides the unit and the method for reliable detection of oil products which may appear in the controlled area and they will be described hereinafter in a more detail.

Figure 1:
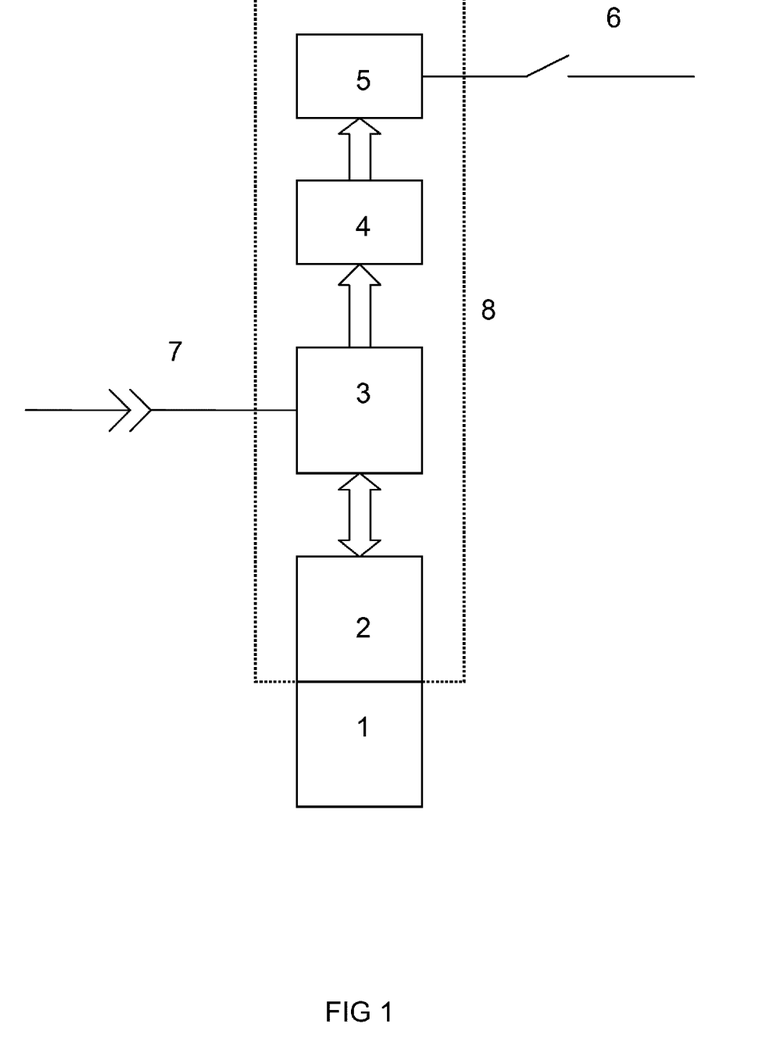
FIG. 1 shows an electro-mechanical block-scheme of the unit according to the present invention.

In FIG. 1 is shown electro-mechanical block-scheme of the unit. The unit includes opto-electronic unit 2 (hereinafter—"sensor") that is provided with a protective snoot 1 and connected to electronic compartment 3 (FIG. 1). Sensor is followed by microprocessor controller 4 with embedded software for carrying out necessary analyses of reflected signals received by sensor. The controller 4 is connected to communication means 5 for transmitting an alarm signal through external communication line 6 in case of oil pollution. Considered communication means may be any contact or wireless communication line supported by microcontroller, namely LAN, RS485, Radio Link, Wi-Fi, GSM, Bluetooth, or any other custom solution. The waterproof and hermetic housing can be also filled with neutral gas at overpressure, providing additional safety of exploitation and protecting optical and electronic components from condensed humidity.

Microprocessor controller provides instant analysis of collected signals and communication means deliver the observation result, and more specifically—an alarm, when oil pollution is detected. All the above elements of the unit may be supplied from an external power supply 7 and are accommodated into a waterproof housing 8.

FIG. 2 shows a first version of an optical layout of the sensor according to the invention. When describing different versions of the sensor the same elements in figures are designated with the same reference numbers.

The sensor according to the invention includes pulsed UV LED 10; collimating optics 10', narrow band optical filter 20; dichroic mirror 30; projection-receiving lens 40; optical filter 50; photodetector 60 and reference photodetector 70.

The sensor according to the invention operates as follows. At first the LED (FIG. 2) is switched ON and it emits a pulse of light in UV spectral range with duration $\tau_0$, and this pulse is collimated with corresponding optical system 10', 20 and directed to the water surface through dichroic mirror 30 and the lens 40. The long-pass dichroic mirror 30 serves to reflect the LED emission at the wavelength $\lambda_{LED}$ and to pass the light with the wavelengths longer than $\lambda_{cut}$ through the filter (at the condition that $\lambda_{LED} < \lambda_{cut}$). The mirror 30 is used also to align the LED beam to be coaxial with the optical axis of receiving lens 40. Then the UV LED pulse hits the water and induces the fluorescence of constituents in it.

The light flux returned from the water contains scattered light at the wavelength $\lambda_{LED}$ and induced fluorescence in the spectral range $\lambda_{fl} > \lambda_{cut}$. The lens 40 serves to shape the fluorescence flux within preset divergence to provide optimal cut-off performance of the filter set 50. The fluorescence is collected by the receiving lens 40 and spectrally filtered by the dichroic mirror 30. The cut off wavelength $\lambda_{cut}$ is selected such that the fluorescence of oil products passes through the mirror 30. The long pass filter 50 is used to select the fluorescence flux caused by oil products in specific spectral ranges and to suppress all other spectral components in the return light flux.

For example, when the incident fluorescence flux has a divergence lower than 3 degrees, the filter will pass less than 1% of light below cut-off wavelength and 90% with longer wavelengths. At higher divergence the filter will pass 10% of light below cut-off wavelength thus mixing the fluorescence flux with excitation light at the detector 60.

The filtered fluorescence flux is registered by the photo-detector 60 by integrating the return signal in a time interval $\tau_1$ synchronously with the LED pulse (at the condition that $\tau_1 \geq \tau_0$).

Next the LED is switched off and the photo-detector 60 registers the background signal due to the ambient light by integrating such light collected by the lens 40 and passed through the mirror 30 and long pass filter 50 during the same time interval $\tau_1$. Further subtraction of the background signal from the signal of induced fluorescence eliminates the influence of ambient light to the sensor operation for oil detection.

This two-step measuring procedure is repeated N times (N≥1) to produce resulting fluorescence value with subtracted background due to ambient light as an accumulated signal per N pulses of LED. The procedure of signal accumulation serves to increase the SNR at the photodetector 60.

The reference detector 70 is used to register the energy of LED pulse and to normalize the return signal by its value to eliminate any variations of detected fluorescence flux caused by fluctuations of LED intensity in time due to environmental factors, work resource, etc.

The alarm of oil detection is done by the microprocessor controller 4 (FIG. 1) which compares the intensity of the accumulated signal with the pre-defined threshold value based on the signal of clean water registered according to the two-step procedure described above. The alarm is reported through the external communication line 6 (FIG. 1).

There are several possible configurations of the detection part of the sensor. In the first option the filter 50 could be of multi band design to pass the fluorescence flux to the detector 60 in several specific spectral ranges. For example in such layout one spectral band can be selected to pass the fluorescence flux of light oil products, the next one—for medium oils, and another one—for heavy oil products.

Figure 3:
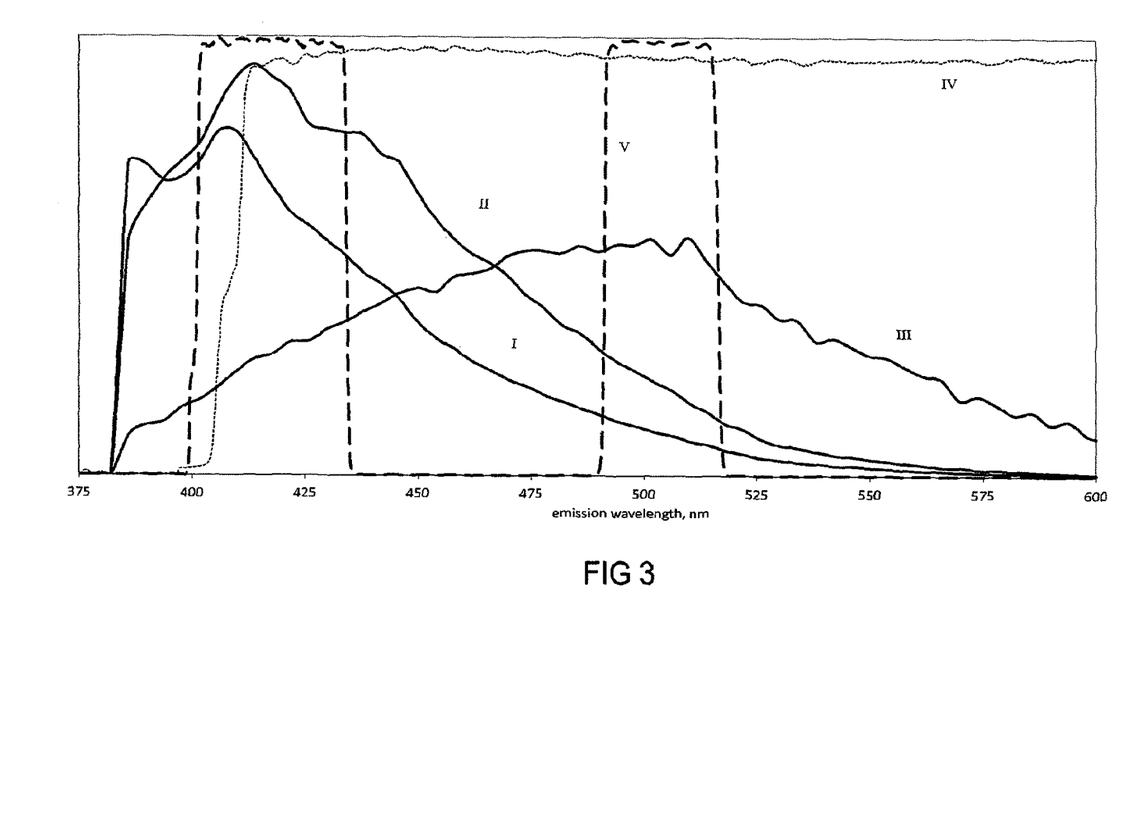
FIG. 3 shows the fluorescence spectra of light, medium and heavy oil respectively and transparency curves of dichroic and long pass filters.

In FIG. 3 a fluorescence spectra of light (I), medium (II) and heavy (III) oil in water at the excitation wavelength 350 nm are shown. Transparency curve of dichroic filter is indicated by reference number IV and transparency curve of dual long pass filter is indicated by reference number V, respectively.

In this case any type of oil product will give the signal to the detector non-selective towards different oil types. The fluorescence outside of the spectral ranges will be not taken into account, thus minimizing the false alarm rate.

Figure 4:
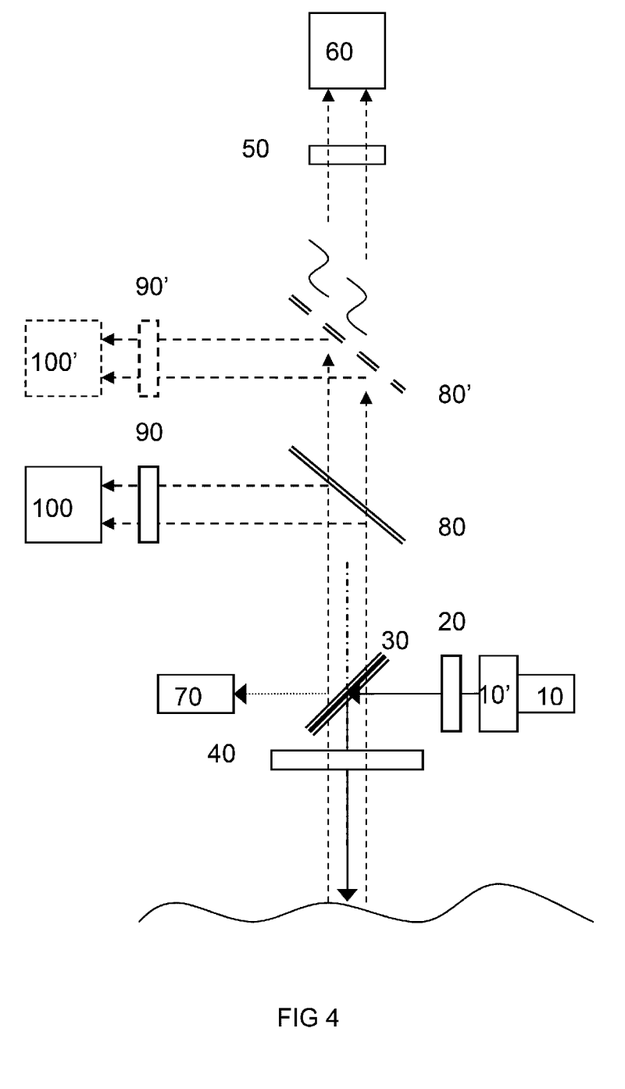
FIG. 4 shows second version of the optical layout of the sensor according to the invention.

In FIG. 4 there is shown more complex optical layout of the sensor, whereby reference number 10 designates pulsed UV LED, 10'—collimating optics, 20—narrow band optical filter, 30—dichroic mirror, 40—projection-receiving lens, 50—long pass optical filter, 60—photodetector, 70—reference photodetector, 80—beam splitter for the second detection channel, 80'—optical beam splitter for one more detection channels, 90, 90'—different optical filters, and 100, 100'—photodetectors, respectively.

In this layout of the detection part of the sensor unit the fluorescence flux collected by the lens 40 is split into several beams (channels) by the beam splitter 80, 80' positioned along the optical axis of the lens 40, everyone of which is followed by detector assembly consisting of photo-detector 60 coupled with narrow band filter 50. Such detection scheme allows detection of spectral signals in different spectral ranges by a separate detector, thus providing selective information of the spectral range generating the alarm, thus providing better differentiation of the signals due to oil from other materials.

Figure 5:
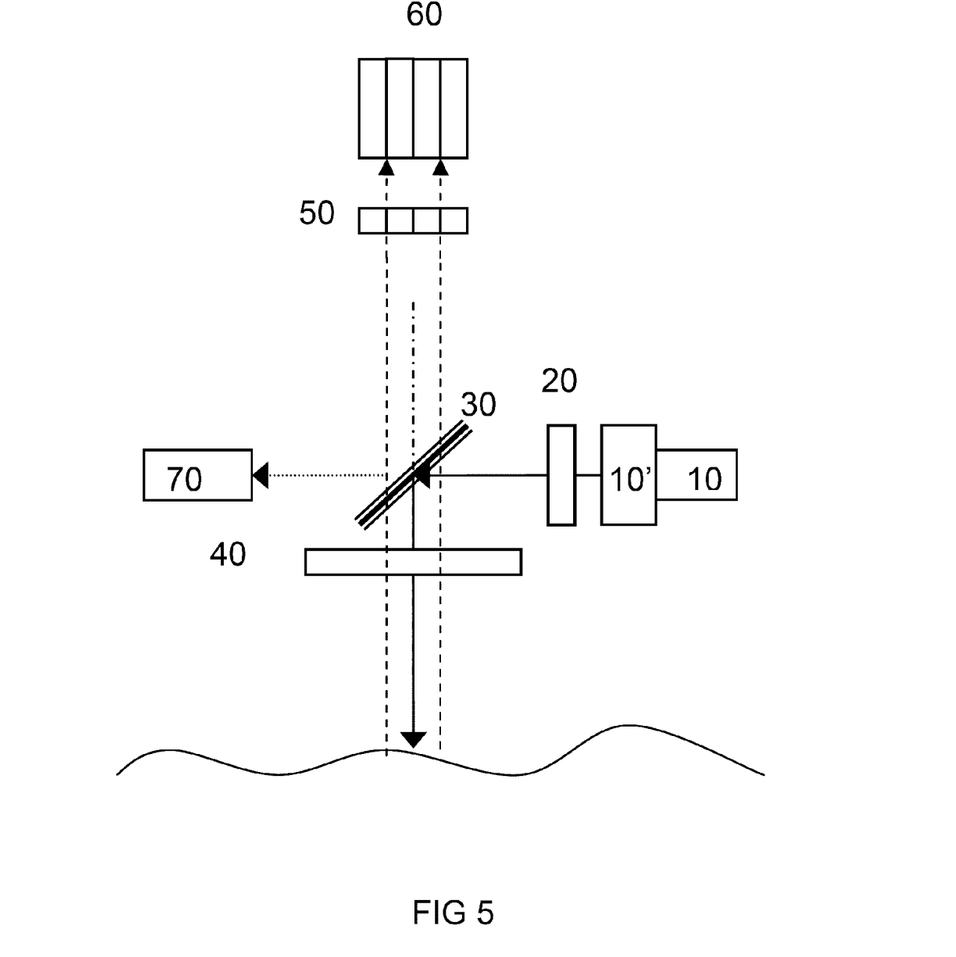
FIG. 5 shows third version of the optical layout of the sensor according to the invention.

In FIG. 5 there is shown yet another optical layout of the sensor, whereby reference number 10 designates pulsed UV LED, 10'—collimating optics, 20—optical filter, 30—dichroic mirror, 40—receiving lens, 50—assembly of optical filters, 60—assembly of photodetectors and 70—reference photodetector, respectively.

The detector can also consist of the assembly of photodetectors 60 like an array or a matrix of narrow band spectral filters 50 in front of every detector element of N photodetectors aligned with the set of optical filters 50. Such an assembly is aligned with the optical lens 40 and, when exposed to the fluorescence flux, will provide multichannel spectral detection of the fluorescence. In this scheme even more detail spectral information for differentiation of oil signal from other materials can be obtained. This kind of selective spectral information of the fluorescence signal minimizes the false alarm rate.

The use of pulsed UV LED as a sensing light source delivers a number of benefits. Due to its small size (almost a point light source) it is possible to design a compact optical scheme with minimal losses of the energy at signal detection. Besides that the sensing beam has low divergence providing longer sensing distance at lower power consumption comparing with other light sources. As described above, the pulsed mode of light source operation synchronized with the detector is important in eliminating the influence of the ambient light to the detector. Due to high pulse repetition rate (PRR) of LED (up to 1 kHz) it is possible to realize data sampling and background subtraction accumulated per number of LED pulses (accumulation mode) to improve SNR at the detector.

While the LED light has narrow spectral width, the filter 2 (FIG. 5) serves to make the excitation monochromatic in order to provide better separation of excitation light and fluorescence flux.

Figure 6:
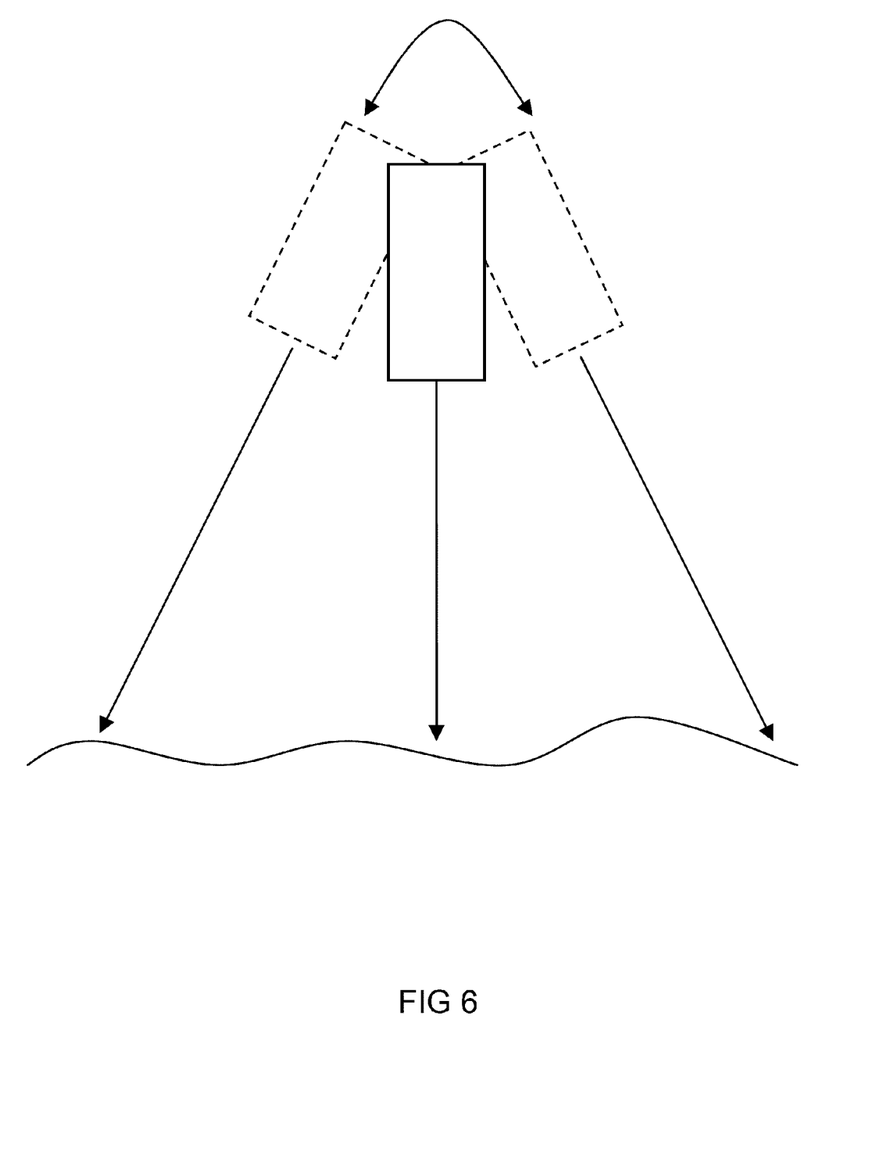
FIG. 6 are shown operational positions of the unit inclined from vertical in scanning mode.

By using dichroic mirror it is possible to realize compact coaxial design of the sensor. Due to aligned optical axes of the sensing beam and the optical lens 4 the sensor operation does not depend on the inclination angle from vertical position. It is particularly important for on-shore and on buoy installations to monitor adjacent water surfaces. This feature is of principal importance for providing sensing of water with scanning the light beam as indicated in FIG. 6. The unit is scannable up to 45 degrees from the vertical position.

The LED with several emission wavelengths can be used in the layouts shown in FIGS. 5 and 6. When the emission wavelength is controlled, separate detection channels serve to register the fluorescence at different excitation wavelengths, thus providing even better differentiation of oil fluorescence from any other signals.

Synchronous with LED high frequency data sampling by the detector gives the possibility to differentiate the short-term and long-term variations of the signal at the detector, providing additional information for decision making and increasing the reliability of alarm generation. Using a solid state detector in combination with LED allows low voltage sensor operation, and it reduces the risk in its application in highly explosive fire-hazardous environments (e.g. oil terminals, pipelines, off-shore platforms).

Low power consumption makes possible long-time sensor operation with storage or solar batteries. This feature is of great importance for sensors installed for autonomous operations without power lines available.

The method of oil detection according to present invention is based on the registration of the integral intensity of fluorescence emission in the spectral ranges defined by detector configuration and recorded as an accumulated difference of the intensity $I_1$ of the return light flux during the LED pulse and without it (i.e. $I_2$).

In this way the background signal due to ambient light is not taken into account. When the accumulated signal exceeds the pre-defined threshold $I_0$ (i.e. $(<I_2-I_1>)><I_0>$), the microcontroller produces the alarm signal. The threshold may be defined as an averaged intensity of the sensor signal over M pulses of LED recorded from the clean water after sensor installation on-site.

Figure 7:
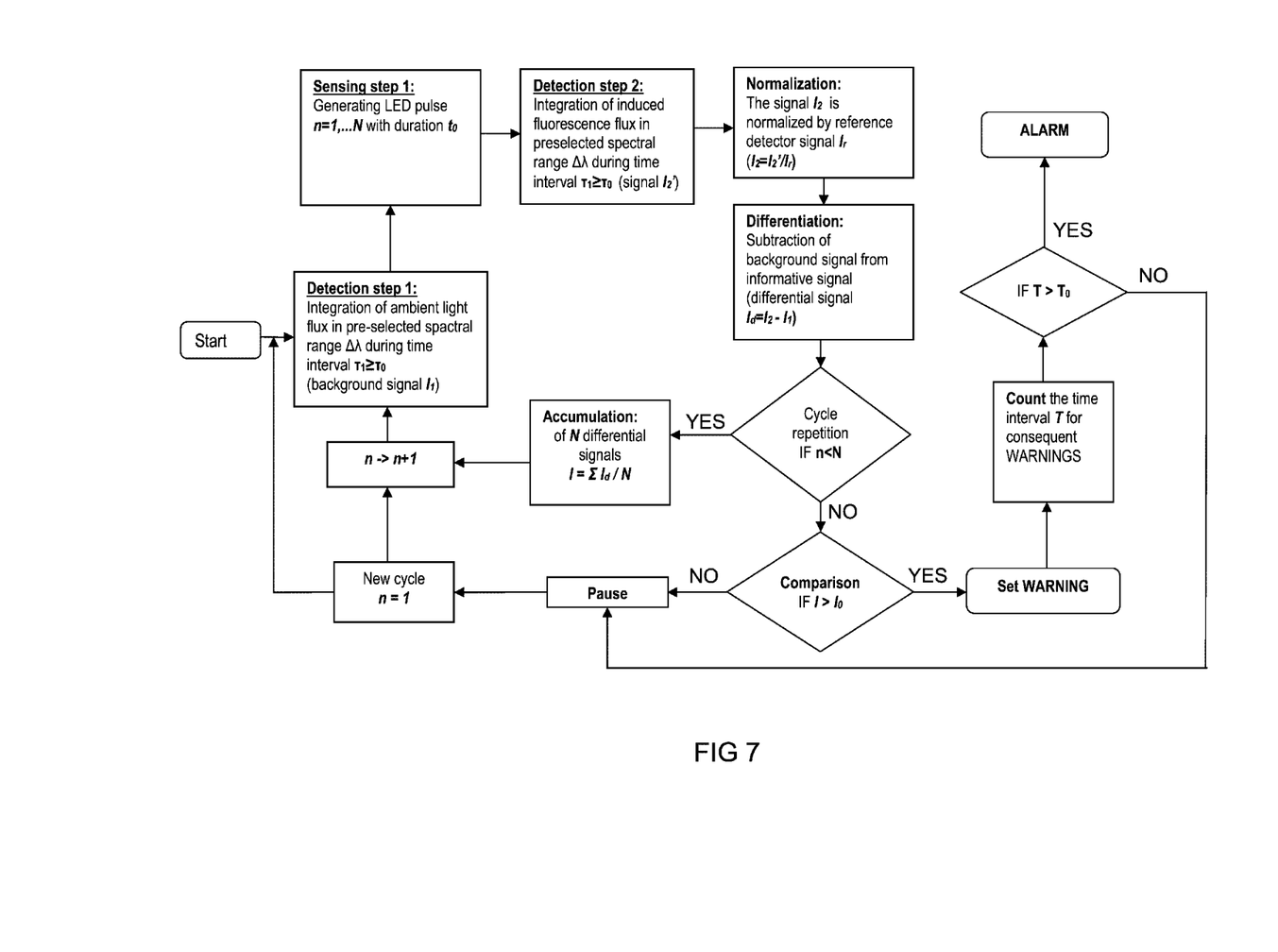
FIG. 7 shows a flow chart of the method according to the present invention.

The flow chart of the method of oil detection is shown in FIG. 7. The process starts with measuring the ambient light flux in the preselected spectral range(s) $\Delta\lambda$ defined by the configuration of filter sets 50, 90 and 90' respectively in FIGS. 2, 4 and 5. The background signal $I_1$ on the detector is integrated during time interval $\tau_1$. The latter is defined by the duration of the LED light pulse by the condition $\tau_1 > \tau_0$. Then the LED pulse is generated. The detector records the return light signal $I'_2$ synchronously with the LED light pulse in the same preselected spectral range(s) $\Delta\lambda$ during the same time interval $\tau_1$. Simultaneously the reference detector records the signal $I_r$ proportional to light flux of LED. Then the signal $I'_2$ is normalized by $I_r$ and the informative signal $I_2$ is produced. After that the background signal $I_1$ is subtracted from informative signal $I_2$ resulting in the differential signal $I_d = I_2 - I_1$. The differential signal is accumulated during the cycle of preset number of LED pulses N: $I = \Sigma I_d / N$. If accumulated signal I exceeds the threshold $I_0$ the system sets the warning status. The threshold signal $I_0$ is defined by described measuring procedure when the water surface is supposed to be in normal conditions (clean), e.g. after on-site installation of the sensor. The time of continuous warning status is counted by the system, and when its duration exceeds the threshold $\tau_0$, the system reports an alarm.

The time $\tau_0$ is defined by application requirements. By taking into account the sizes of oil patches and the flow velocity in the controlled area, it is possible to set-up the reasonable "alarm generation time". For example, if the oil patch of 1 m size is considered as noticeable, and the flow velocity in the area is 0.5 m per second, then such patch will remain in the field of view of the sensor during 2 seconds. In this time frame the sensor operating at the sampling rate 10 Hz will provide 20 continuous warning signals providing statistical confirmation for reporting alarm. Such analysis of detected signals with optimized PRR, accumulation time and alarm generation time according to on-site conditions lowers the risk of false alarms by filtering off single instantaneous variations exceeding the threshold for warning.

The accumulation of signal per N pulses of LED usually provides SNR increase by root of number N. For example signal accumulation per 100 LED pulses at the pulse frequency 100 Hz will increase SNR by order of magnitude in 1 sec time interval. From one hand such time is reasonably short and allows detection of small oil patches even in water with strong current. From the other hand, analysis of 100 signals recorded inside accumulation time allows excluding the short time spikes of the signal caused by other reasons or objects. Such analysis of detected signals with optimized PRR and accumulation time according to on-site conditions lowers the risk of false alarm by filtering off single instantaneous variations exceeding the threshold.

In case of multichannel detection specified in FIGS. 4 and 5 the flow chart according to FIG. 7 is equally performed for every single detection channel synchronously with the LED pulse. As a result, the threshold signal 10 is defined individually for every detection channel, and exceeding such threshold provides selective information of the spectral range generating the alarm, thus better differentiating the signals due to oil from other materials.

When the detection configuration with several channels is used, the method of data analysis compares the difference in signals in defined spectral channels influenced by oil products with the corresponding values of the signal in other detection channels influenced by other organic materials in water to distinguish oil product appearance in the waters with variable organic content (i.e. run-off, waste or other industrial waters). This increases the reliability of oil detection.

The invention is not limited to the embodiments described above and there may be made various changes and modifications not deviating from the scope of appended claims.

The invention claimed is:

1. A unit for optical non-contact continuous remote detection of presence of light, medium and heavy oil products on a water surface or in a water column, said unit comprising:
a sensor, wherein the sensor is connected to an electronic compartment followed by a microprocessor controller with embedded software for carrying out analyses of reflected signals received by the sensor, the microprocessor controller is connected to communication means for transmitting an alarm signal through an external communication line in case of oil pollution, wherein all the above elements are supplied by external power supply and accommodated into a waterproof housing,
wherein said sensor comprises a probe light source formed by a pulsed UV LED coupled with a collimating optics and a narrow band optical filter,
said sensor further comprising at least one dichroic mirror, a projection-receiving lens, at least one photodetector, at least one optical filter for each at least one photodetector, and a reference photodetector,
wherein a probe light beam generated by the UV LED is guided by the collimating optics through the narrow band optical filter onto the dichroic mirror,
wherein at least one part of said probe light beam is passed through said dichroic mirror into the reference photodetector for registering an intensity signal of the probe light beam generated by the UV LED,
wherein said dichroic mirror deflects a major part of said probe light beam through the projection-receiving lens onto the water surface such that said deflected probe light beam is coaxial with the axis of said projection-receiving lens, and
wherein a return light from the water surface is passed to said at least one photodetector through said projection-receiving lens, through said dichroic mirror, and through said at least one optical filter for each at least one photodetector.

2. The unit according to claim 1, wherein a cut off wavelength of the dichroic mirror is selected such that the dichroic mirror reflects UV LED light pulses having a wavelength in a UV spectral region shorter than the cut off wavelength of the dichroic mirror and passes through the return light in a spectral region of longer wavelengths than the cut off wavelength of the dichroic mirror.

3. The unit according to claim 1, wherein the at least one optical filter at each photodetector is a multi band long pass optical filter passing through induced fluorescent flux of light, medium and heavy oil products simultaneously and suppressing all other spectral components in the return light flux.

4. The unit according to claim 1, wherein the sensor comprises at least two separate photodetectors, each photodetector having its own optical filter, said optical filters being long pass optical filters,
wherein the return light is divided for each of said corresponding photodetectors by at least one beam splitter and a differential signal of the two separate photodetectors in a spectral range limited by two cut-off wavelengths of the long pass optical filters registers induced fluorescence of specified light, medium or heavy oil products by corresponding selection of the cut off wavelengths.

5. The unit according to claim 1, wherein the sensor unit comprises three separate photodetectors, each photodetector is coupled with an optical filter, said optical filters being narrow band optical filters,
wherein the passing spectral ranges of said narrow band optical filters are selected such that a first narrow band optical filter coupled with a first photodetector passes through induced fluorescence flux in a spectral range for light oil products, a second narrow band optical filter coupled with a second photodetector passes through induced flux in a spectral range for medium oil products, and a third optical filter coupled with a third photodetector passes through induced fluorescence flux in a spectral range for heavy oil products.

6. The unit according to claim 1, wherein the at least one photodetector comprises an assembly of photodetector elements in an array, wherein each photodetector element is aligned with an optical filter at said photodetector for providing multichannel spectral detection of the fluorescence.

7. The unit according to claim 1, wherein the unit is scannable up to 45 degrees from a vertical position.

8. The unit according to claim 1, wherein the waterproof housing of the unit is filled with gas at overpressure for additional safety of exploitation.

9. The unit according to claim 1, wherein the UV LED of the unit emits light at a single wavelength or at multiple wavelengths in a controlled mode.

10. The unit according to claim 1, wherein the UV LED is controlled to switch, with the time interval $\tau 1$, between emitting the LED pulse and being turned off, wherein the at least one photodetector records the return light from the water surface synchronously with LED pulse in a preselected spectral range $\Delta\lambda$ during a time interval $\tau 1$ while the UV LED is emitting the LED pulse, wherein the at least one photodetector registers background signals due to ambient light by integrating the ambient light collected by the projection-receiving lens and passed through the dichroic mirror and the at least one optical filter during the time interval τ1 while the UV LED is off, and wherein the time interval τ1 is equal to or greater than a duration of the LED pulse τ0.

11. The unit according to claim 1, wherein a cut off wavelength of the dichroic mirror is selected such that the dichroic mirror reflects UV LED light pulses having a wavelength in a UV spectral region shorter than the cut off wavelength of the dichroic mirror and passes through the return light in a spectral region of longer wavelengths than the cut off wavelength of the dichroic mirror, and wherein the projection-receiving lens is configured to shape fluorescence flux in the return light within a divergence of lower than 3 degrees.

12. A method for optical non-contact continuous remote detection of presence of oil products on a water surface or in a water column, wherein probe light beam pulses are generated and guided through optics onto the water, and return light reflected from the water surface is guided through the optics into a sensor unit for registering signals, wherein the method comprises the following steps:
- integrating ambient light flux in a preselected spectral range(s) Δλ by a photodetector during time interval $\tau_1$ and obtaining a background signal $I_1$, wherein the time interval $\tau_1$ is defined by a duration of UV LED light pulse $\tau_0$ by a condition $\tau_1 > \tau_0$;
- continuously generating a preset number of probe light beam pulses with duration to with the UV LED and guiding said probe light beam pulses by-collimating optics through an optical filter onto a dichroic mirror;
- passing a part of each of said probe light beam pulse generated by the UV LED through said dichroic mirror into a reference photodetector for registering a signal ($I_r$) proportional to the intensity of the probe light flux generated by the UV LED pulse;
- deflecting coaxially a major part of each probe light beam pulse generated by the UV LED with an axis of a projection-receiving lens by said dichroic mirror through said projection-receiving lens onto the water surface as a low divergent light beam;
- synchronously with each probe light beam pulse, collecting and passing a return light signal by the projection-receiving lens through said dichroic mirror onto a detector means for registering the return light signal;
- producing a return light informative signal by normalizing return light signal using a reference signal of the reference photodetector;
- subtracting background light signal from the return light informative signal in order to obtain a differential signal;
- obtaining and accumulating during cycles differential signal levels as a signal and comparing with a predetermined threshold signal level, and if signal exceeds threshold signal level, sending a warning; and
- if a counted time interval of consequent warnings exceeds a preset time interval $T_0$ set for consequent warning status, generating the alarm signal.

* * * * *